United States Patent [19]
Fischetti et al.

[11] Patent Number: 5,556,944
[45] Date of Patent: Sep. 17, 1996

[54] IMMUNOGLOBULIN A BINDING PROTEIN

[75] Inventors: Vincent A. Fischetti, West Hampstead, N.Y.; Debra E. Bessen, Woodbridge, Conn.

[73] Assignee: Rockefeller University, New York, N.Y.

[21] Appl. No.: 330,515

[22] Filed: Oct. 3, 1994

Related U.S. Application Data

[62] Division of Ser. No. 813,584, Dec. 24, 1991, Pat. No. 5,352,588.

[51] Int. Cl.$^6$ .......................... C07K 14/315; C07K 17/00
[52] U.S. Cl. .......................... 530/350; 530/402; 435/69.1
[58] Field of Search .................................... 530/350, 324, 530/331, 402; 514/2; 424/484, 486; 435/69.1, 320.1

[56] References Cited

U.S. PATENT DOCUMENTS 4,757,134  7/1988  Blake et al. .
5,210,183  5/1993  Lindahl et al. .

FOREIGN PATENT DOCUMENTS 0367890  5/1990  European Pat. Off. .

OTHER PUBLICATIONS

Lehninger, A. L. (1975) *Biochemistry*, 2nd Ed., New York: Worth; p. 73.

Lancefield, R. C. (1962) "Current Knowledge of Type–Specific M Antigens of Group B Streptococci" *J. Immunol.* 89:307–313.

Frithz, E., L. O. Heden, G. Lindahl (1989) "Extensive sequence homology between IgA receptor and M proteins in *Streptococcus pyogenes*" *Molecular Microbiology* 3(8):1111–1119.

Bessen, D., K. F. Jones, V. A. Fischetti (1989) "Evidence for Two Distinct Classes of Streptococcal M Protein and Their Relationship to Rheumatic Fever" *J. Exp. Med.* 169:269–283.

Bessen, D. E., V. A. Fischetti (1990) "Differentiation Between Two Biologically Distinct Classes of Group A Streptococci by Limited Substitutions of Amino Acids within the Shared Region of M Protein–like Molecules" *J. Exp. Med.* 172:1757–1764.

Bessen, D., V. A. Fischetti (1990) "A Human IgG Receptor of Group A Streptococci Is Associated with Tissue Site of Infection and Streptococcal Class" The Journal of Infectious Diseases 161:747–754.

Khandke, K. M. et al. (1986) "Complete Amino Acid Sequence of Streptococcal PepM49 Protein, A Nephritis–associated Serotype" The Journal of Biological Chemistry 263(11):5075–5081.

Bessen, D. E., V. A., Fischetti (1992) "Nucleotide Sequences of Two Adjacent M or M–Like Protein genes of Group A Streptococci: Different RNA Transcript Levels and Identification of a Unique Immunoglobulin A–Binding Protein" Infection and Immunity 60(1):124–135.

Haanes, E. J., P. P. Clearly (1989) "Identification of a Divergent M Protein Gene and an M Protein–Related Gene Family in *Streptococcus pyogenes* Serotype 49" Journal of Bacteriology 171(12):6397–6408.

Jeppson, H., E. Frinthz, L.–O. Heden (1992) "Duplication of a DNA sequence homologous to genes for immunoglobulin receptors and M proteins in *Streptococcus pyogenes*"FEMS Microbiology Letters 92:139–146.

*Primary Examiner*—Garnette D. Draper
*Assistant Examiner*—David L. Fitzgerald
*Attorney, Agent, or Firm*—Saliwanchik & Saliwanchik

[57] ABSTRACT

The subject invention concerns a novel polynucleotide sequence cloned from emm2.2 gene of a Group A streptococcus, Type II strain which codes for an IgA-binding protein,ML2.2. The subject invention further concerns the novel IgA-binding protein. A process for producing the protein is given. The invention also concerns the protein in an immunoadsorbent and as a tracer for use in measuring and purifying IgA. Kits are given comprising the immunoadsorbent and the tracer form of the protein.

6 Claims, 2 Drawing Sheets

IMMUNOGLOBULIN A BINDING PROTEIN

CROSS-REFERENCE TO A RELATED APPLICATION

This application is a division of application Ser. No. 07/813,584, filed Dec. 24, 1991, now U.S. Pat. No. 5,352,588.

This invention concerns a gene coding for a novel immunoglobulin A (IgA) binding protein from group A streptococci of Class II, a process for producing the protein by genetic recombination and the use of the protein to capture and measure IgA.

BACKGROUND OF THE INVENTION

Group A streptococci are responsible for a wide variety of human diseases, the most common of which are nasopharyngitis and impetigo. Nearly all clinical isolates have the antiphagocytic factor, M protein, on their surface. This virulence factor displays extreme antigenic diversity within its amino-terminal region. It is these highly variable portions of M proteins which form the basis of the serological typing scheme which was formulated in the 1930s prior to knowledge of any structural detail (Lancefield, R. C., *J. Immunol.* 89:307–313 (1962)).

In recent years, the sequences of M or M-like proteins have been reported (Frithz, E., Heden, L. O. and Lindahl, G. *Mol. Microbiol.* 3:1111 (1989)). The M-like molecules are structurally similar to M proteins in that they exhibit significant levels of sequence homology; however, they are not considered to be M protein itself because an antiphagocytic property has not been formally demonstrated.

Group A streptococci can be divided into two major classes partly on the basis of their immunoreactivity with a pair of monoclonal antibodies directed to epitopes which lie within the relatively conserved half of M proteins (Bessen, D. and Fischetti, V. A. *J. Exp. Med.* 172:1757 (1990); Bessen, D., Jones, K. F. and Fischetti, V. A. *J. Exp. Med.* 169:269 (1989)). Class I isolates are defined as those binding one or both monoclonal antibodies, whereas class II isolates do not bind either monoclonal antibody. In addition, the classes differ in their ability to exhibit opacity factor activity, and in several pathogenic properties of these organisms (Bessen, D. and Fischetti, V. A. *J. Infect. Dis.* 161:747 (1990)). For example, nearly all serotypes found in association with major outbreaks of rheumatic fever are class I. The classes also differ in ability to bind IgA, with this activity being specific for class II. Obviously this property is important to the function of streptococci as the arp4 protein reported by Lindahl et al. (European Patent Application 367890), e.g., is from class II streptococci and the IgA-binding protein of Russell-Jones et al. (U.S. Pat. No. 4,757,134) is from group B streptococci.

Immunoglobulin A is an important component of the bodily response to pathogens and other disorders. An early mucosal immune response to invasion is production of antibodies of the A class and as a result, elevated levels of IgA can be found in extracts of infected membranes such as saliva, urine, feces and urogenital extracts. Certain disorders such as kidney or liver malfunctions and early cancer detection may also be correlated to IgA. Indeed the human body produces more IgA daily than any other antibody class.

Accordingly, reagents to capture and measure IgA have been sought.

SUMMARY OF THE INVENTION

Two M or M-like protein genes were cloned from a single streptococcus A class II isolate. It was discovered that the product of the downstream gene, hereinafter termed ML2.2, is a protein that exhibits IgA-binding activity. Described herein is a novel process for producing high quantities of this IgA binding protein hereinafter referred to as ML2.2.

The polynucleotide of the present invention comprises DNA of approximately 1.6 kb which codes for a polypeptide having the ability to bind IgA. The polypeptide is an approximately 36 to 42 kD protein expressed by a Group A streptococcus of the IIb class, or a fragment or equivalent of the protein. The polynucleotide has the DNA sequence given in SEQ ID NO. 1. The amino acid sequence of the protein product of the polynucleotide is also given in SEQ ID NO. 3. Most especially the present invention sets forth the polynucleotide sequence which codes for a polypeptide which binds IgA.

The present invention further concerns a plasmid comprising this polynucleotide sequence, preferably plasmid pML2-14.

According to the process of the subject invention, microorganisms which have been transformed with the gene coding for ML2.2 produce and secrete large quantities of the recombinant protein. Specifically, according to the subject invention, a suitable host, an *Escherichia coli*, for example, can be transformed with 1.6 kb DNA comprising the nucleotide sequence shown in SEQ ID NO. 1. This sequence codes for the IgA binding protein of approximately 42,000 daltons designated ML2.2, whose amino acid sequence is also shown in SEQ ID NOS. 1 and 3.

The product of this process, ML2.2, may be used to detect the presence of IgA in a biological sample. To detect IgA, the sample is contacted with the protein under conditions for suitable for reaction, in the presence of suitable buffers and salts, for example, to bind IgA to the protein and the bound product is observed.

Most preferably the protein of the present invention is affixed to a solid surface, a microtiter plate, for example, or an inert bead such as polystyrene or latex to form an immunoadsorbent for removing IgA from a biological sample. IgA may be removed from a sample by contacting the sample with the immunoadsorbent under conditions which allow IgA to bind to the immunoadsorbent. Microtiter plates, for example, may be coated with the protein or beads may be packed into a column through which sample may be passed.

The present invention also sets forth a process for preparing essentially pure IgA from a biological sample, serum, for example, containing IgA. In this process the sample is then contacted with the immunoadsorbent comprising the protein of the present invention, allowing IgA in the sample to bind to the immunoadsorbent. The bound IgA is washed, preferably with a suitable buffer, to remove associated proteins and other contaminants. Finally IgA itself is eluted from the immunoadsorbent by buffers, electroelution or other method known to the art.

In preferred embodiments of the present invention, the protein is conjugated to a group suitable for being observed. Any such groups known to persons skilled in the art may be used. Enzymes such as alkaline phosphatase or peroxidase, metals such as gold or a member of the biotin-avidin binding pair may be used as labels.

The present invention also sets forth kits comprising immunoadsorbent wherein the protein of the present invention is affixed. Kits may also comprise the protein of the present invention labeled for use as tracers.

DETAILS OF THE INVENTION

Figure 1:
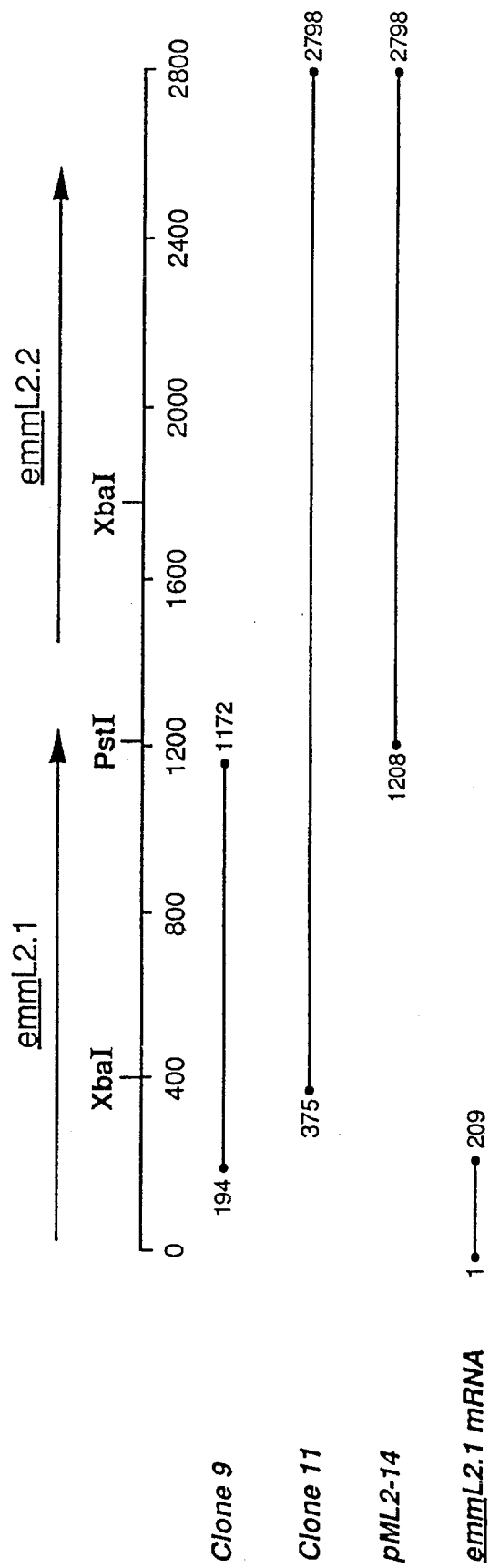
FIG. 1 the region of the T2/MR chromosome cloned and sequenced to produce the nucleotide sequence of SEQ ID NO. 1. Arrows indicate the coding regions of emmL2.1 and emmL2.2. Positions of streptococcal DNA that were cloned into the M13mp19 (inserts from clones 9 and 11) and pUC18 (pML2-14) vectors used for sequencing are shown.

This invention provides a novel recombinant protein and a novel gene and methods for producing this protein. The novel recombinant protein, and subfragments thereof, have affinity for IgA and can be used in a variety of assays and kits.

One aspect of the subject invention is a gene coding for a recombinant protein. The nucleotide sequence of this gene is shown in SEQ ID NO. 1. SEQ ID NOS. 1 and 3 also show the deduced amino acid sequence of the recombinant protein encoded by the gene shown in SEQ ID NO. 1.

The invention further concerns a recombinant polynucleotide sequence comprising a vector in which a DNA sequence coding for the subject recombinant protein, or a fragment thereof, expressible in a suitable host has been inserted. Thus, said vector encodes the novel IgA binding protein and/or a fragment of this protein with substantially the same binding properties to immunoglobulin A. Specifically, the vector may be chosen from plasmids, phage DNA, or derivatives or fragments thereto, or combinations of plasmids and phage DNA and yeast plasmids.

The invention also concerns a host infected, transformed, or transfected with a recombinant DNA molecule comprising a vector in which a DNA sequence coding for the desired protein, or fragment thereof, expressible is a suitable host has been inserted. The inserted DNA is characterized in that the DNA sequence codes for the recombinant IgA binding protein and/or a fragment of this protein with substantially the same binding properties to immunoglobulin A. Among the many suitable hosts that can be infected, transformed, or transfected with the recombinant DNA molecule according to the invention and thereby express this protein or fragments thereof are Gram-positive or negative bacteria such as E. coli, Bacillus subtilis, insect cells and yeast cells.

The various methods employed in the preparation of the plasmids and transformation of host organisms are well known in the art. These procedures are all described in Maniatis, T., E. F. Fritsch, and J. Sambrook (1982) *Molecular Cloning: A Laboratory Manual*, Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, e.g., E. coli cells, prepare plasmid DNA, electrophorese proteins, and sequence DNA.

The DNA sequence of the subject invention can be most readily obtained by a person skilled in the art by isolating said DNA from Group A streptococcal strain T2/44/RB4/119, the M2 typing strain from the Lancefield collection (The Rockefeller University). The nucleotide sequences disclosed herein can also be prepared by a "gene machine" by procedures well known in the art. This is possible because of the disclosure of the nucleotide sequence.

As is well known in the art, the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. The amino acid sequences of the recombinant IgA binding protein and fragments thereof, of the subject invention can be prepared by nucleotide sequences other than that which is shown in SEQ ID NO. 1. Functionally equivalent nucleotide sequences encoding the novel amino acid sequence of these proteins and fragments can be prepared by known synthetic procedures. Accordingly, the subject invention includes such functionally equivalent nucleotide sequences.

Thus the scope of the subject invention includes not only the specific nucleotide sequences depicted herein, but also all equivalent nucleotide sequences coding for molecules with substantially the same antigenic, immunogenic, or therapeutic activity.

Further, the scope of the subject invention is intended to cover not only the specific amino acid sequences disclosed, but also similar sequences of proteins or protein fragments having comparable biological activity.
Preparation of nucleotide.

Randomly sheared chromosomal DNA, derived from a low hemolytic colony of strain T2/44/RB4/119 termed T2/MR (type 2, class II) was cloned into lambda gt11 through EcoRI linkers and partially sequenced (Bessen, D., V. A. Fischetti [1990] *J. Infect. Dis.* 161:747–754). Plaques were first screened with anti-ColiM6 and then with M2 typing sera. Two clones were obtained: clones 9 and 11. Purified lambda gt11 replicative-form DNA containing inserts were subcloned into both M13mp19 and pUC18 vectors (FIG. 1). The insert from clone 11 was subcloned into pUC18 to generate pML2-11. The 1.6 kb PstI-EcoRI fragment derived from pML2-11 was ligated into pUC18 to construct pML2-14.

Nucleotide accession number: the nucleotide sequence encompassing the gene emmL2.2 coding for the IgA binding protein of the present invention is available from EMBL/GenBank/DDJB under accession number X61276. DNA sequence for the polynucleotide coding for protein ML2.2 is submitted on a floppy disk with the present specification.
Purification of polypeptide.

Purification of a 34.5 kD fragment of ML2.2, containing IgA-binding activity was performed by growing E. coli containing pML2-14 to mid-log, and preparing a periplasmic fraction. The fraction was dialyzed in buffer containing protease inhibitors and then contacted with MonoQ and washed in 0.05M Tris (pH 8) containing 0.005M EDTA. The protein was in fall-through fraction.

The protein was affinity purified with immobilized human myeloma IgA and then eluted with glycine, pH 2.0. The first eluted fractions were re-applied to the column. Eluants were dialyzed and concentrated. Final purification was obtained by contacting eluant with mono-S in 0.05M NaOAc, pH 5.5 and 0.005M EDTA. Elution was obtained in buffer containing gradient up to 1.0M NaCl.

DNA sequencing.

Foreign DNA cloned into M13 and pUC vectors was sequenced by the dideoxy-chain termination method. Overlapping inserts were generated in M13mp19 by T4 polymerase digestion. Streptococcal DNA cloned into pUC18 vectors was sequenced because of the inability to clone the sense strand of major portions of insert 11 into M13 bacteriophage. The DNA sequence of pML2-14 is given in SEQ ID NO. 1.

Figure 2:
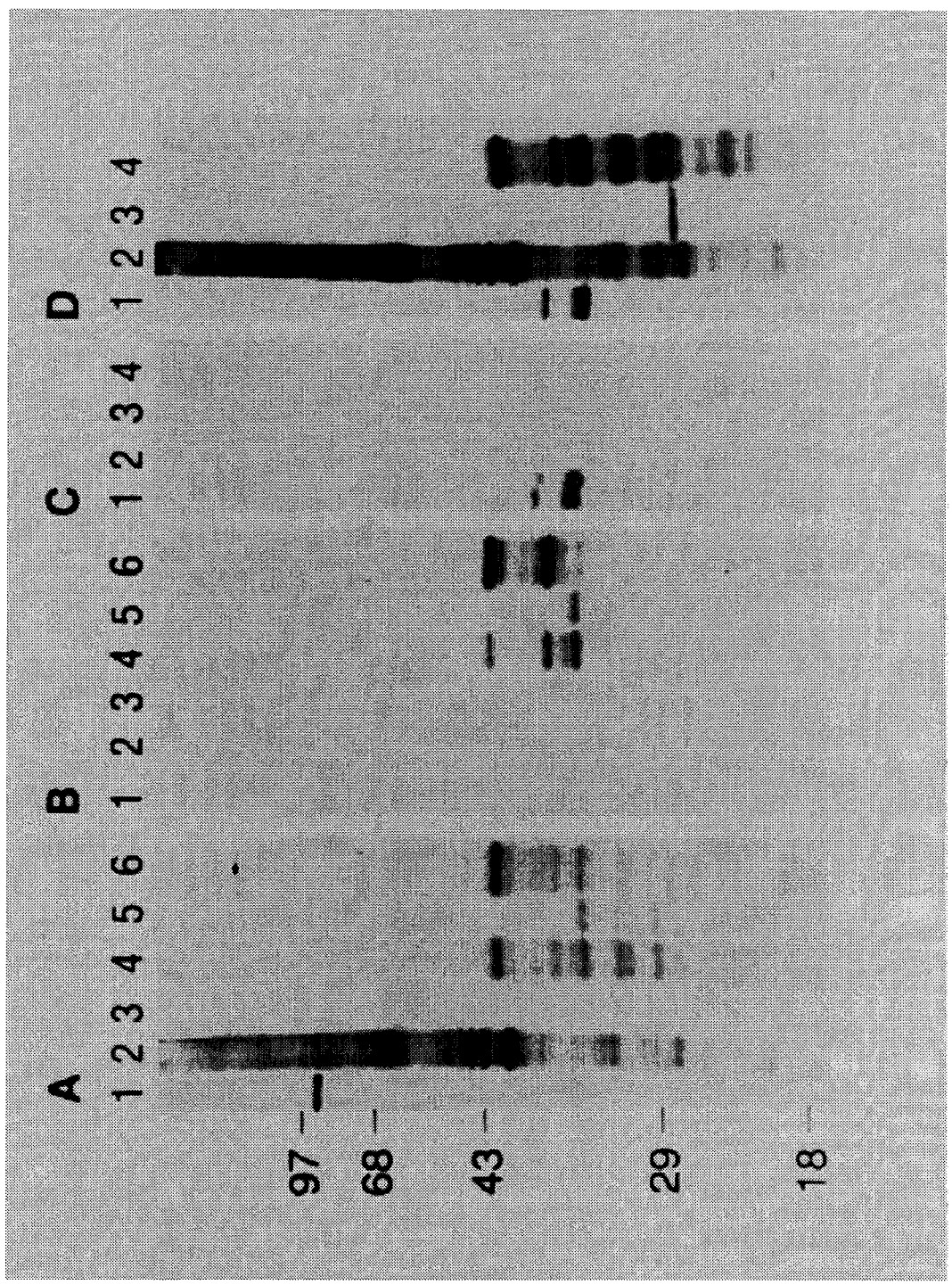
FIG. 2 gives the Western blot analysis of the cloned emmL2.2 gene product. Lanes 1 contain lysin extract of 29452, a streptococcal strain (type 22, class II) obtained from the Institute of Hygiene and Epidemiology, Prague, Czechoslovakia, Lanes 2 contain lysin extract of T2/MR, a M-rich isolate of Group A streptococcal strain T2/44/RB4/119 (Class II) from the Lancefield collection (The Rockefeller University), Lanes 3 contain whole E. coli XL-1 cells and Lanes 4 contain whole E. coli XL-1 cells harboring pML2-14. Blot A is anti-coil6, blot B is human myeloma IgA, blot C is human IgG-Fc fragment and blot D is anti-peptide d240 to 260. The positions of molecular size markers (in kD) are shown to the left.

The longest open reading frame for the emmL2.2 gene extends from nucleotide 1452 to 2567. The first 41 amino acids are homologous to signal peptides of other M and M-like proteins (Frithz, E., L. -O. Heden, G. Lindahl [1989] *Mol. Microbiol.* 3:1111–1119; Gomi, H., T. Hozumi, S. Hattori, C. Tagawa, F. Kishimoto, L. Bjorck [1990] *J. Immunol.* 144:4046–4052). Therefore, the mature emmL2.2 gene product is expected to be 331 residues with a predicted molecular weight of 36,769; this size is in reasonable accordance with the 42 kD band expressed by *E. coli* harboring pML2-14 (FIG. 2, Lane 4). There is a single region of sequence repeats in the ML2.2 protein, consisting of three 23-residue C repeat segments separated by two spacers (spanning amino acids 90 to 203).

Sequence identities.

Amino acids 1 through 71 of the mature ML2.2 protein sequence display only very limited homologies to the ML2.1 protein located upstream or with other M and M-like molecules. According to maximal alignment of sequences by the Protalign algorithm, there is 53% amino acid sequence identity between ML2.1 and ML2.2 proteins, and the homology is located for the most part within their carboxy-terminal two-thirds. ML2.2 protein exhibits 82% homology to the deduced sequence of ennX, an M-protein of unknown function (Haanes, E. J., P. P. Cleary [1989] *J. Bacteriol.* 171:6397–6408) and appears to be transcriptionally silent in streptococci (Cleary, P. P., D. LaPenta, D. Heath, E. J. Haanes, C. Chen [1991] "A virulence region in *Streptococcus pyogenes*," In *Genetics and Molecular Biology of Streptococci, Lactococci, and Enterococci* (G. M. Dunny, P. P. Cleary, L. L. McKay, eds.), American Society for Microbiology, Washington, D.C., pp. 147–151). Arp4 and ML2.2, both IgA-binding proteins, are only 56% identical in sequence, despite their similar functions.

Binding properties of ML2.2 protein.

Whole cell lysates of *E. coli* harboring pML2-14 bind human myeloma IgA by Western blotting (FIG. 2, Lane 4). The gene product expressed by pML2-14 displayed several bands, many of which are likely degradation products of the major band at 42 kilodalton. Whole *E. coli* cells having no pML2-14 do not bind IgA. Also the lysin extract of streptococcal strain 29452 does not bind IgA although intact cells do bind IgA.

The emmL2.2 gene product, ML2.2 protein, fails to bind the class I-specific monoclonal antibodies which recognize epitopes in the C repeat regions of class I molecules.

The Ig-binding sites within M and M-like molecules have not been identified. The three M or M-like immunoglobulin binding proteins cloned and sequenced to date (Arp4, ProtH and ML2.2) have in common class II-like C repeat regions (Bessen and Fischetti [1990], supra) and subtleties within the class II C repeat may influence Ig-binding.

It should be understood that the examples and embodiments described herein are for illustrative purposes only and that various modifications or changes in light thereof will be suggested to persons skilled in the art and are to be included within the spirit and purview of this application and the scope of the appended claims.

---

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1560 base pairs
        ( B ) TYPE: nucleic acid
        ( C ) STRANDEDNESS: single
        ( D ) TOPOLOGY: unknown ( i i ) MOLECULE TYPE: DNA (genomic)

( i x ) FEATURE:
        ( A ) NAME/KEY: CDS
        ( B ) LOCATION: 2..40

( i x ) FEATURE:
        ( A ) NAME/KEY: CDS
        ( B ) LOCATION: 252..1367

( x i ) SEQUENCE DESCRIPTION: SEQ ID NO:1:

```
A TCT GCA GGT ATG CTT GCT CTA AAA CGC AAA GAA GAA AAC TAAGCATTAG        50
  Ser Ala Gly Met Leu Ala Leu Lys Arg Lys Glu Glu Asn
  1               5                   10

ACTGATGCTA AAGCTAAGAG AGAATCAAAT GATTCTCTCT TTTTGAGTGG CTAAGTAACT     110

AACAATCTCA GTTAGACCAA AAAATGGGAA TGGTTCAAAA AGCTGGCCTT TACTCCTTTT     170
```

```
GATTAACCAT ATATAATAAA AACATTAGGA AAATAATAGT AATATTAAGT TTGTTTCCTC    230

AATAAAATCA AGGAGTAGAT A ATG GCT AGA CAA CAA ACC AAG AAA AAT TAT    281
             Met Ala Arg Gln Gln Thr Lys Lys Asn Tyr
              1                5                  10

TCA CTA CGA AAA CTA AAA ACC GGT ACG GCT TCA GTA GCC GTT GCT TTG    329
Ser Leu Arg Lys Leu Lys Thr Gly Thr Ala Ser Val Ala Val Ala Leu
         15              20                  25

ACC GTT TTG GGC GCA GGT TTT GCA AAC CAA ACA GAA GTA AGA GCT GAT    377
Thr Val Leu Gly Ala Gly Phe Ala Asn Gln Thr Glu Val Arg Ala Asp
             30              35                  40

GAA GCT AAA AAA ATG GAA GTA AAA GAA AGT GAA AAA GAG TCC CAG TAT    425
Glu Ala Lys Lys Met Glu Val Lys Glu Ser Glu Lys Glu Ser Gln Tyr
         45              50                  55

AAG ACG TTG GCT TTA AGA GGT GAA AAT GCT GAC CTT AGA AAT GTA AAT    473
Lys Thr Leu Ala Leu Arg Gly Glu Asn Ala Asp Leu Arg Asn Val Asn
         60              65                  70

GCA AAA TAT TTA GAG AAA ATT AAC GCA GAA GAA GAA AAA AAT AAA AAG    521
Ala Lys Tyr Leu Glu Lys Ile Asn Ala Glu Glu Glu Lys Asn Lys Lys
75              80                  85                  90

CTT GAA GCA ATT AAT AAA GAG CTA AAT GAG AAT TAT TAC AAA TTA CAG    569
Leu Glu Ala Ile Asn Lys Glu Leu Asn Glu Asn Tyr Tyr Lys Leu Gln
             95                  100                 105

GAT GGC ATT GAT GCT CTA GAA AAA GAA AAA GAA GAT CTC AAA ACA ACT    617
Asp Gly Ile Asp Ala Leu Glu Lys Glu Lys Glu Asp Leu Lys Thr Thr
             110                 115                 120

TTA GCT AAG ACT ACT AAA GAA AAT GAG ATT TCA GAA GCT AGC CGT AAA    665
Leu Ala Lys Thr Thr Lys Glu Asn Glu Ile Ser Glu Ala Ser Arg Lys
         125                 130                 135

GGG TTA AGC CGA GAC TTA GAA GCT TCT CGT ACA GCT AAA AAA GAG CTA    713
Gly Leu Ser Arg Asp Leu Glu Ala Ser Arg Thr Ala Lys Lys Glu Leu
     140                 145                 150

GAA GCT AAG CAT CAA AAA TTA GAA GCA GAA AAC AAA AAA CTA ACA GAA    761
Glu Ala Lys His Gln Lys Leu Glu Ala Glu Asn Lys Lys Leu Thr Glu
155                 160                 165                 170

GGC AAT CAG GTT TCA GAA GCT AGT CGT AAA GGT CTA AGT AAC GAC TTA    809
Gly Asn Gln Val Ser Glu Ala Ser Arg Lys Gly Leu Ser Asn Asp Leu
             175                 180                 185

GAA GCT TCT CGT GCA GCT AAA AAA GAA CTA GAA GCT AAG TAC CAA AAA    857
Glu Ala Ser Arg Ala Ala Lys Lys Glu Leu Glu Ala Lys Tyr Gln Lys
             190                 195                 200

TTA GAG ACT GAT CAC CAA GCC CTA GAA GCT AAG CAC CAA AAA TTA GAG    905
Leu Glu Thr Asp His Gln Ala Leu Glu Ala Lys His Gln Lys Leu Glu
         205                 210                 215

GCT GAT TAC CAA GTT TCA GAG ACT AGC CGT AAG GGT CTA AGT CGT GAC    953
Ala Asp Tyr Gln Val Ser Glu Thr Ser Arg Lys Gly Leu Ser Arg Asp
         220                 225                 230

CTT GAA GCG TCT CGT GAA GCT AAT AAG AAG GTT ACA TCT GAG TTA ACA    1001
Leu Glu Ala Ser Arg Glu Ala Asn Lys Lys Val Thr Ser Glu Leu Thr
235                 240                 245                 250

CAA GCA AAA GCT CAA CTC TCA GCG CTT GAA GAA AGT AAG AAA TTA TCA    1049
Gln Ala Lys Ala Gln Leu Ser Ala Leu Glu Glu Ser Lys Lys Leu Ser
                 255                 260                 265

GAA AAA GAA AAA GCT GAG TTA CAA GCA AAA CTA GAT GCA CAA GGA AAA    1097
Glu Lys Glu Lys Ala Glu Leu Gln Ala Lys Leu Asp Ala Gln Gly Lys
             270                 275                 280

GCC CTC AAA GAA CAA TTA GCA AAA CAA ACT GAA GAG CTT GCA AAA CTA    1145
Ala Leu Lys Glu Gln Leu Ala Lys Gln Thr Glu Glu Leu Ala Lys Leu
         285                 290                 295

AGA GCT GAA AAA GCG GCA GGT TCA AAA ACA CCT GCT ACC AAA CCA GCT    1193
Arg Ala Glu Lys Ala Ala Gly Ser Lys Thr Pro Ala Thr Lys Pro Ala
```

-continued

```
                  300                           305                           310
AAT  AAA  GAA  AGA  TCA  GGT  AGA  GCT  GCT  CAA  ACA  GCT  ACA  AGA  CCT  AGC       1241
Asn  Lys  Glu  Arg  Ser  Gly  Arg  Ala  Ala  Gln  Thr  Ala  Thr  Arg  Pro  Ser
315                 320                      325                           330

CAA  AAT  AAA  GGA  ATG  AGA  TCA  CAA  TTA  CCG  TCA  ACA  GGC  GAA  GCA  GCT       1289
Gln  Asn  Lys  Gly  Met  Arg  Ser  Gln  Leu  Pro  Ser  Thr  Gly  Glu  Ala  Ala
                    335                      340                      345

AAC  CCA  TTC  TTT  ACA  GCA  GCA  GCT  GCA  ACA  GTG  ATG  GTA  TCT  GCT  GGT       1337
Asn  Pro  Phe  Phe  Thr  Ala  Ala  Ala  Ala  Thr  Val  Met  Val  Ser  Ala  Gly
               350                           355                      360

ATG  CTT  GCT  CTA  AAA  CGC  AAA  GAA  GAA  AAC  TAAGTCTTTA  GAACTTGGTT             1387
Met  Leu  Ala  Leu  Lys  Arg  Lys  Glu  Glu  Asn
               365                 370

TTTGTAACGG  TGCAATAGAC  AAAAGCAAGC  AAGGCAAAA  ACTGAGAAAG  TCCTAAAAAG                1447

CTGGCCTTTA  CCCCTAAAAA  TTAATGTTTT  ATAATAAAGA  TGTTAGTAAT  ATAATTGATA               1507

AATGAGATAC  ATTTAATCAT  TATGGCAAAA  GCAAGAAAAA  TAGCTGTATC  ATA                      1560
```

( 2 ) INFORMATION FOR SEQ ID NO:2:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ser  Ala  Gly  Met  Leu  Ala  Leu  Lys  Arg  Lys  Glu  Glu  Asn
1                   5                        10
```

( 2 ) INFORMATION FOR SEQ ID NO:3:

( i ) SEQUENCE CHARACTERISTICS:
        ( A ) LENGTH: 372 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met  Ala  Arg  Gln  Gln  Thr  Lys  Lys  Asn  Tyr  Ser  Leu  Arg  Lys  Leu  Lys
1                   5                        10                      15

Thr  Gly  Thr  Ala  Ser  Val  Ala  Val  Ala  Leu  Thr  Val  Leu  Gly  Ala  Gly
                    20                       25                      30

Phe  Ala  Asn  Gln  Thr  Glu  Val  Arg  Ala  Asp  Glu  Ala  Lys  Lys  Met  Glu
               35                       40                      45

Val  Lys  Glu  Ser  Glu  Lys  Glu  Ser  Gln  Tyr  Lys  Thr  Leu  Ala  Leu  Arg
     50                  55                           60

Gly  Glu  Asn  Ala  Asp  Leu  Arg  Asn  Val  Asn  Ala  Lys  Tyr  Leu  Glu  Lys
65                       70                      75                      80

Ile  Asn  Ala  Glu  Glu  Lys  Asn  Lys  Lys  Leu  Glu  Ala  Ile  Asn  Lys
                         85                  90                           95

Glu  Leu  Asn  Glu  Asn  Tyr  Tyr  Lys  Leu  Gln  Asp  Gly  Ile  Asp  Ala  Leu
                    100                      105                     110

Glu  Lys  Glu  Lys  Glu  Asp  Leu  Lys  Thr  Thr  Leu  Ala  Lys  Thr  Thr  Lys
               115                           120                     125

Glu  Asn  Glu  Ile  Ser  Glu  Ala  Ser  Arg  Lys  Gly  Leu  Ser  Arg  Asp  Leu
          130                      135                          140

Glu  Ala  Ser  Arg  Thr  Ala  Lys  Lys  Glu  Leu  Glu  Ala  Lys  His  Gln  Lys
145                      150                          155                     160
```

|   |   |   |   |   |   |   |   |   |   |   |   |   |   |   |
|---|---|---|---|---|---|---|---|---|---|---|---|---|---|---|
| Leu | Glu | Ala | Glu | Asn<br>165 | Lys | Lys | Leu | Thr | Glu<br>170 | Gly | Asn | Gln | Val | Ser<br>175 | Glu |
| Ala | Ser | Arg | Lys<br>180 | Gly | Leu | Ser | Asn | Asp<br>185 | Leu | Glu | Ala | Ser | Arg<br>190 | Ala | Ala |
| Lys | Lys | Glu<br>195 | Leu | Glu | Ala | Lys | Tyr<br>200 | Gln | Lys | Leu | Glu | Thr<br>205 | Asp | His | Gln |
| Ala | Leu<br>210 | Glu | Ala | Lys | His | Gln<br>215 | Lys | Leu | Glu | Ala | Asp<br>220 | Tyr | Gln | Val | Ser |
| Glu<br>225 | Thr | Ser | Arg | Lys | Gly<br>230 | Leu | Ser | Arg | Asp | Leu<br>235 | Glu | Ala | Ser | Arg | Glu<br>240 |
| Ala | Asn | Lys | Lys | Val<br>245 | Thr | Ser | Glu | Leu | Thr<br>250 | Gln | Ala | Lys | Ala | Gln<br>255 | Leu |
| Ser | Ala | Leu | Glu<br>260 | Glu | Ser | Lys | Lys | Leu<br>265 | Ser | Glu | Lys | Glu | Lys<br>270 | Ala | Glu |
| Leu | Gln | Ala<br>275 | Lys | Leu | Asp | Ala | Gln<br>280 | Gly | Lys | Ala | Leu | Lys<br>285 | Glu | Gln | Leu |
| Ala | Lys<br>290 | Gln | Thr | Glu | Glu | Leu<br>295 | Ala | Lys | Leu | Arg | Ala<br>300 | Glu | Lys | Ala | Ala |
| Gly<br>305 | Ser | Lys | Thr | Pro | Ala<br>310 | Thr | Lys | Pro | Ala | Asn<br>315 | Lys | Glu | Arg | Ser | Gly<br>320 |
| Arg | Ala | Ala | Gln | Thr<br>325 | Ala | Thr | Arg | Pro | Ser<br>330 | Gln | Asn | Lys | Gly | Met<br>335 | Arg |
| Ser | Gln | Leu | Pro<br>340 | Ser | Thr | Gly | Glu | Ala<br>345 | Ala | Asn | Pro | Phe | Phe<br>350 | Thr | Ala |
| Ala | Ala | Ala<br>355 | Thr | Val | Met | Val | Ser<br>360 | Ala | Gly | Met | Leu | Ala<br>365 | Leu | Lys | Arg |
| Lys | Glu<br>370 | Glu | Asn |   |   |   |   |   |   |   |   |   |   |   |   |

We claim:

1. A purified polypeptide, wherein said polypeptide comprises residues 42 through 372 of the amino acid sequence shown in SEQ ID NO: 3, and wherein said polypeptide is capable of specifically binding with an IgA antibody.

2. The polypeptide, according to claim 1, having the amino acid sequence shown in SEQ ID NO. 3.

3. A purified polypeptide according to claim 1, having the sequence shown as residues 42 through 372 of SEQ ID NO: 3.

4. The polypeptide of claim 1 immobilized on an inert support.

5. The polypeptide, according to claim 1, wherein said polypeptide is that polypeptide which is obtained when the plasmid pML2-14 is expressed in a microorganism.

6. The polypeptide, according to claim 5, wherein said microorganism is *E. coli*.

* * * * *

UNITED STATES PATENT AND TRADEMARK OFFICE
CERTIFICATE OF CORRECTION

PATENT NO. : 5,556,944
DATED : September 17, 1996
INVENTOR(S) : Vincent A. Fischetti and Debra E. Bessen It is certified that error appears in the above-indentified patent and that said Letters Patent is hereby corrected as shown below:

Column 3, Line 5: "FIG. 1 the region" should read --FIG. 1 gives the region--;
Column 3, Line 20: "Blot A is anti-coil6," should read --Blot A is anti-coli6--.

Signed and Sealed this

Twenty-eighth Day of January, 1997

Attest:

BRUCE LEHMAN

Attesting Officer    Commissioner of Patents and Trademarks